United States Patent
Costa da Cruz

(10) Patent No.: US 9,888,976 B2
(45) Date of Patent: Feb. 13, 2018

(54) REMOTE PATIENT MONITORING AND MEDICATION DELIVERY SYSTEM

(71) Applicant: FUNDAÇÃO D. ANNA DE SOMMER CHAMPALIMAUD E DR. CARLOS MONTEZ CHAMPALIMAUD, Lisbon (PT)

(72) Inventor: José António Almeida Costa da Cruz, Lisbon (PT)

(73) Assignee: FUNDAÇÃO D. ANNA DE SOMMER CHAMPALIMAUD E DR. CARLOS MONTEZ CHAMPALIMAUD, Lisbon (PT)

( * ) Notice: Subject to any disclaimer, the term of this patent is extended or adjusted under 35 U.S.C. 154(b) by 0 days.

(21) Appl. No.: 15/377,933

(22) Filed: Dec. 13, 2016

(65) Prior Publication Data
US 2018/0008360 A1    Jan. 11, 2018

(30) Foreign Application Priority Data
Jul. 8, 2016  (PT) .......................................... 109515

(51) Int. Cl.
*A61B 50/13*    (2016.01)
*A61B 50/18*    (2016.01)
(Continued)

(52) U.S. Cl.
CPC .............. *A61B 50/13* (2016.02); *A61B 5/002* (2013.01); *A61B 5/02055* (2013.01);
(Continued)

(58) Field of Classification Search
CPC ............. G06F 19/3456; G06F 19/3462; G06F 19/322; G06F 19/3418; A61J 7/0076; A61J 7/04; A61J 7/0409; A61J 7/0436; A61J 7/0445; A61J 7/0481; A61J 7/049; A61B 50/13; A61B 50/18; A61B 5/002;
(Continued)

(56) References Cited

U.S. PATENT DOCUMENTS

2009/0014458 A1*  1/2009  Heffron ............... A61G 12/001 221/2
2012/0218123 A1   8/2012  Ji et al.
(Continued)

FOREIGN PATENT DOCUMENTS

EP      1 197 178 A1       4/2002
WO      WO 00/06018 A1     2/2000
WO      WO 2008/141283 A2  11/2008

OTHER PUBLICATIONS

International Search Report and Written Opinion in corresponding PCT Application No. PCT/IB2017/054082, dated Oct. 17, 2017.

*Primary Examiner* — Hai Phan
*Assistant Examiner* — Franklin Balseca
(74) *Attorney, Agent, or Firm* — Leason Ellis LLP

(57) ABSTRACT

The present invention relates to systems and methods for remotely monitoring the health of a patient in a real-time, continuous manner, remotely deliver therapeutic medications to the patient, and facilitating communication between the patient and a remotely located patient care provider.

21 Claims, 13 Drawing Sheets

(51) Int. Cl.
<table>
<tr><td>A61J 7/04</td><td>(2006.01)</td></tr>
<tr><td>A61J 7/00</td><td>(2006.01)</td></tr>
<tr><td>A61B 5/1172</td><td>(2016.01)</td></tr>
<tr><td>A61B 5/1171</td><td>(2016.01)</td></tr>
<tr><td>A61B 5/0205</td><td>(2006.01)</td></tr>
<tr><td>A61B 5/00</td><td>(2006.01)</td></tr>
<tr><td>A61B 5/021</td><td>(2006.01)</td></tr>
<tr><td>A61B 5/024</td><td>(2006.01)</td></tr>
<tr><td>A61B 5/08</td><td>(2006.01)</td></tr>
<tr><td>A61B 5/1455</td><td>(2006.01)</td></tr>
<tr><td>A61G 12/00</td><td>(2006.01)</td></tr>
<tr><td>G06F 19/22</td><td>(2011.01)</td></tr>
<tr><td>G06F 19/00</td><td>(2011.01)</td></tr>
</table>

(52) U.S. Cl.
CPC .......... *A61B 5/1172* (2013.01); *A61B 5/1176* (2013.01); *A61B 5/742* (2013.01); *A61B 5/746* (2013.01); *A61B 50/18* (2016.02); *A61G 12/001* (2013.01); *A61J 7/0076* (2013.01); *A61J 7/0445* (2015.05); *A61J 7/0481* (2013.01); *G06F 19/322* (2013.01); *G06F 19/3418* (2013.01); *G06F 19/3456* (2013.01); *A61B 5/021* (2013.01); *A61B 5/02438* (2013.01); *A61B 5/0816* (2013.01); *A61B 5/14551* (2013.01)

(58) Field of Classification Search
CPC . A61B 5/02055; A61B 5/1172; A61B 5/1176; A61B 5/742; A61B 5/746; A61B 5/021; A61B 5/02438; A61B 5/0816; A61B 5/14551; A61G 12/001
See application file for complete search history.

(56) References Cited

U.S. PATENT DOCUMENTS

| | | | |
|---|---|---|---|
| 2012/0316405 A1* | 12/2012 | Taylor | G06Q 50/24 600/301 |
| 2014/0276549 A1* | 9/2014 | Osorio | A61M 5/1723 604/503 |
| 2015/0119652 A1* | 4/2015 | Hyde | A61B 5/0022 600/301 |

* cited by examiner

REMOTE PATIENT MONITORING AND MEDICATION DELIVERY SYSTEM

FIELD OF THE INVENTION

The present invention generally relates to patient care monitoring. More particularly, the present invention relates to systems and methods for remotely monitoring patient condition in a real-time, continuous manner and remotely dispensing therapeutic medications.

BACKGROUND OF THE INVENTION

Hospitals and other patient care services have on-site doctors, nurses, and other caregivers for monitoring interned patients. Patient care services can only monitor a limited number of patients at one time due to availability of patient beds and monitoring equipment (e.g., vital signs monitors). As such, hospitals have a desire to discharge patients as soon as possible in order to free up space and equipment to receive new patients. However, if a patient is discharged early without further monitoring by the patient care provider, the patient can be at risk of potential latent health complications remaining undiscovered until it is too late. Additionally, if the patient is discharged from the patient care provider, the patient cannot easily receive scheduled or impromptu medication doses from the caregiver. As such, there is a need for remote patient monitoring.

Current remote monitoring solutions employ a variety of vital sign measuring and communication solutions that generally require a wireless hub (e.g., an Internet/Bluetooth connection) connected to a patient's home Internet infrastructure to communicate with a remote central station at the hospital or patient care service. This type of setup requires a lengthy installation and configuration process at the patent's home. Other conventional solutions that employ Internet or Bluetooth technology can suffer from delays or interruptions in transmitting multimedia or vital signs data to the remote central station and thus are unsuitable for real-time, continuous monitoring. Further, a skilled technician, doctor, or nurse is needed at the patient's home to operate the monitoring equipment as a specialist at the remote hospital examines the patient.

It is in regard to these issues and others that the present invention is provided.

BRIEF DESCRIPTION OF THE DRAWINGS

The invention is illustrated in the figures of the accompanying drawings which are meant to be exemplary and not limiting, in which like references are intended to refer to like or corresponding parts, and in which.

SUMMARY AND DETAILED DESCRIPTION OF THE INVENTION

Figure 1:
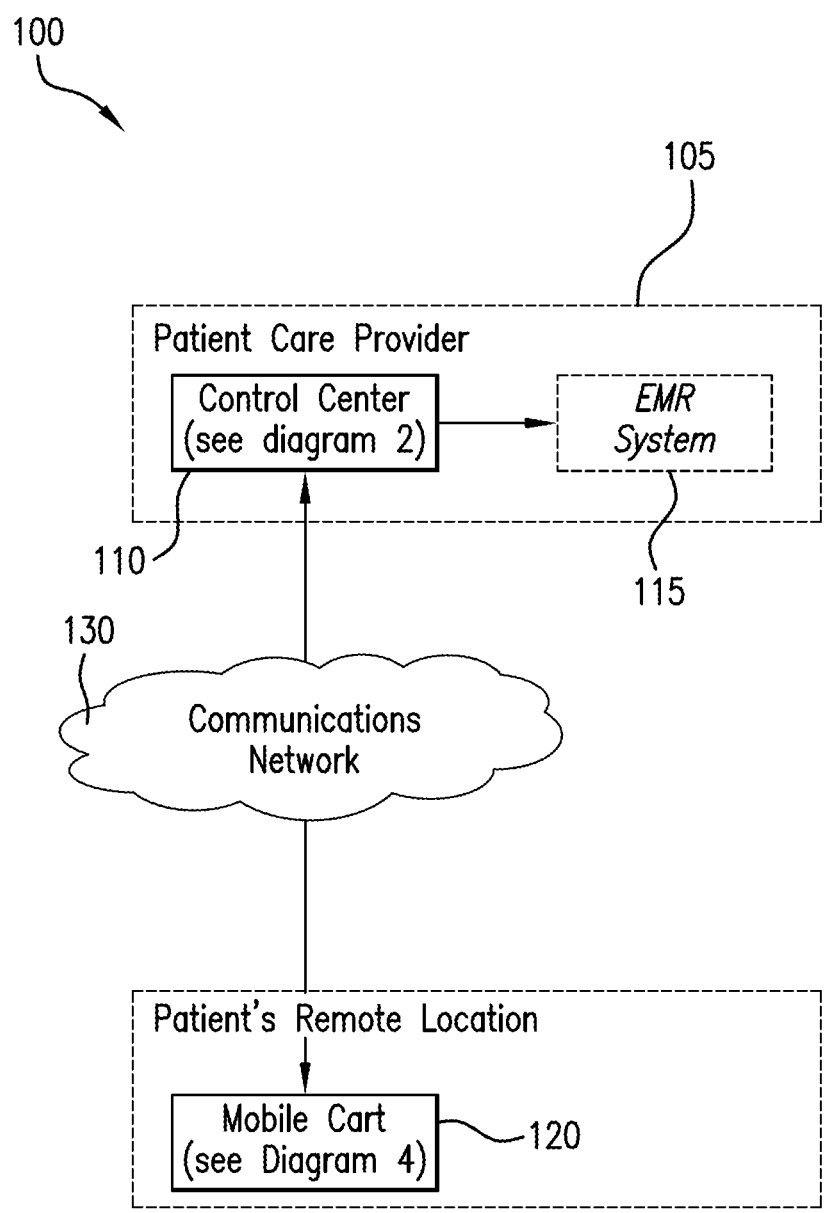
FIG. 1 presents a schematic diagram illustrating a system for remotely monitoring a patient according to one or more implementations of the present invention.

Throughout the specification, terms may have nuanced meanings suggested or implied in context beyond an explicitly stated meaning. Likewise, the phrase "in one implementation" as used herein does not necessarily refer to the same implementation and the phrase "in another implementation" as used herein does not necessarily refer to a different implementation. Similarly, the phrase "one or more implementations" as used herein does not necessarily refer to the same implementation and the phrase "at least one implementation" as used herein does not necessarily refer to a different implementation. The intention is, for example, that claimed subject matter includes combinations of example implementations in whole or in part.

The present disclosure details systems and methods for remotely monitoring a patient's vital signs and status at the patient's bedside, and facilitating communications between the patient and a remote central station located at a hospital or other health care providing service. Though reference is made to implementations in which a hospital is the remote health care providing service, it will be appreciated that the invention is not limited to only remote patient monitoring in conjunction with hospitals, but rather can be implemented in accordance with other caregiver services, health care providers, day care services, care service providers, health care specialist offices, assisted living arrangements, and the like. As such, terminology referring to a patient care provider can interchangeably include "hospital," "health care provider," "caregiver," "nurse" or other similar terms.

As present approaches in the technical field of remote patient monitoring and communication have not been highly effective or efficient in maintaining real-time, continuous vital sign monitoring and communication between a patient and a remote caregiver, while not requiring additional patient-side infrastructure or patient-side professional assistance, the present systems and methods employ a mobile patient information and medication delivery platform comprising hardware, software, and/or a combination of the two to address such needs. Particularly, the systems and methods in one exemplary embodiment include a patient-side monitoring apparatus comprising a mobile cart, a computing device having a processor, a non-transitory processor readable media (i.e., a memory) and one or more data communication subsystems, a modem, a router, one or more media input devices, one or more media output devices, a medication dispenser, and an uninterruptable power supply. In this way, the present invention provides easy to use, accessible, compact and robust equipment for remote patient monitoring.

In one aspect of the invention, the monitoring platform communicates with a remote central station over a mobile communications network (e.g., 3G/4G networks) without needing additional patient-side infrastructure, such as an Internet connection. In one or more implementations, the monitoring platform includes a 3G/4G modem and a network router for establishing a virtual private network (VPN) channel to securely connect to a remote central station for the purpose of transmitting media and vital signs data. The only technical requirements beyond the monitoring platform are electrical power and mobile telecommunications coverage.

With reference now to FIG. 1, a schematic diagram illustrating a mobile patient monitoring and medication delivery system 100 for monitoring and delivering medications to a patient remote from a patient care provider according to one or more implementations of the present invention is provided. Monitoring system 100 includes a patient care provider-side system 105 having a control center 110 for receiving incoming patient vital sign data and facilitating communication with the remote patient, and an electronic medical record (EMR) system 115 that stores patient data. For example, the patient care provider system can be located a hospital or assisted living center. In one or more implementations, current measured patient vital signs data received by patient care provider system 105 can be integrated into existing EMRs stored in a patient care provider database that are associated with the patient. For example, patient care provider system 105 can be configured to be interoperable with existing hospital health care standards or frameworks, such as Health Level Seven Standards (HL7).

Monitoring system 100 also includes a physical patient-side system for monitoring the patient, which can capture media (e.g., video and audio) data, and capture information concerns patent vital signs. In one or more implementations, the patient system is housed in a mobile cart 120 capable of being arranged at any remote patient location. In one or more implementations, the remote patient location is located within the same building as the patient care provider. For example, the caregiver (e.g., a doctor) can be in one wing of a hospital, and the mobile cart 120 can be at the bedside of the patient in a separate wing of the hospital. Mobile cart 120 can include one or more shelves, ledges, racks, mantles, channels, vacancies or other storage locations, in which specific components of monitoring system 100 can be placed such that the patient-side system is disposed entirely at the mobile cart, thereby improving mobility. For example, other components of monitoring system 100 can be disposed fully or partially within the housing of mobile cart 120, located on the outer surfaces of the mobile cart, or otherwise coupled with the mobile cart.

Captured media and vital sign data can be transmitted between patient care provider system 105 and mobile cart 120 across a communications network 130. Both patient care provider system 105 and mobile cart 120 include one or more wireless transceivers, preferably a wireless cellular telephony transceiver (e.g., 1G, 2G, 3G, 4G), or another wireless protocol to connect the mobile cart 120 to the patient care provider system 105 or other device, external component, or a network. While other transceivers, such as an IEEE 802.11 transceiver, an infrared transceiver, or a Bluetooth transceiver can be used with monitoring system 100, certain advantages are provided by use of a mobile telecommunications network, as described elsewhere herein. In one or more implementations, the monitoring system 100 does not require an Internet connection or Bluetooth availability. For example, network 130 can be a mobile telecommunication network (e.g., 3G/4G), which advantageously is not dependent on the local infrastructure of the patient's home. 3G/4G networks are widely available, and thus the mobile cart 120 can avoid requiring an Internet connection or a land line phone at the patient's home. Further, the quality of the communications sent by patient care provider system 105 or mobile cart 120 depends only on the 3G/4G connection and is not impacted by the user infrastructure. Thus, media or vital sign data generated by the patient is not delayed or interrupted because other users are monopolizing the Internet at patient's home to download files, watch videos or listen to music streams.

Figure 2:
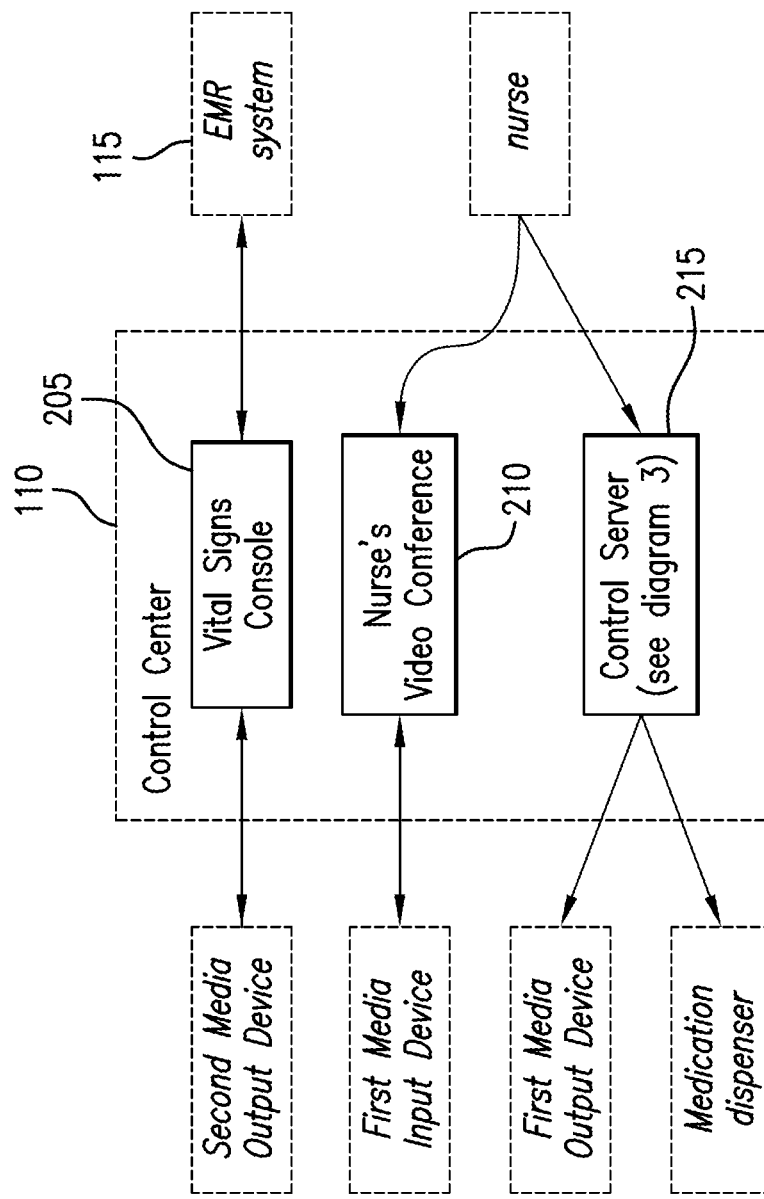
FIG. 2 presents a schematic diagram illustrating a patient care provider-side control center for remotely monitoring a patient according to one or more implementations of the present invention.

With reference now to FIG. 2, the control center 110 of patient care provider-side system 105 includes a vital signs console 205, a nurse video conferencing system 210, and a control server 215. Vital signs console 205 is a general purpose computing device configured to receive signals transmitted by a remote vital signs monitor (e.g., measured by sensors 420 and transmitted by computing device 405, described below) that correspond to measured patient vital signs at the mobile cart 120. Vital signs console 205 is also in connection to EMR system 115, and can automatically process received vital signals and update patient records stored in a database at EMR system 115 in accordance with preexisting health care provider standards (e.g., HL7). In one or more implementations, the vital signs console 205 is capable of processing vital signs pertaining to oximetry, heart rate, temperature, respiratory rate, and blood pressure.

Nurse video conferencing 210 comprises one or more audiovisual input and output devices, such as displays, cameras, microphones, and audio speakers. A patient care provider (e.g., a nurse, assistant, specialist, doctor, etc.) can use nurse video conferencing 210 to capture video and audio to be transmitted to the mobile cart 120, as well as view video and audio captured by the patient.

Figure 3:
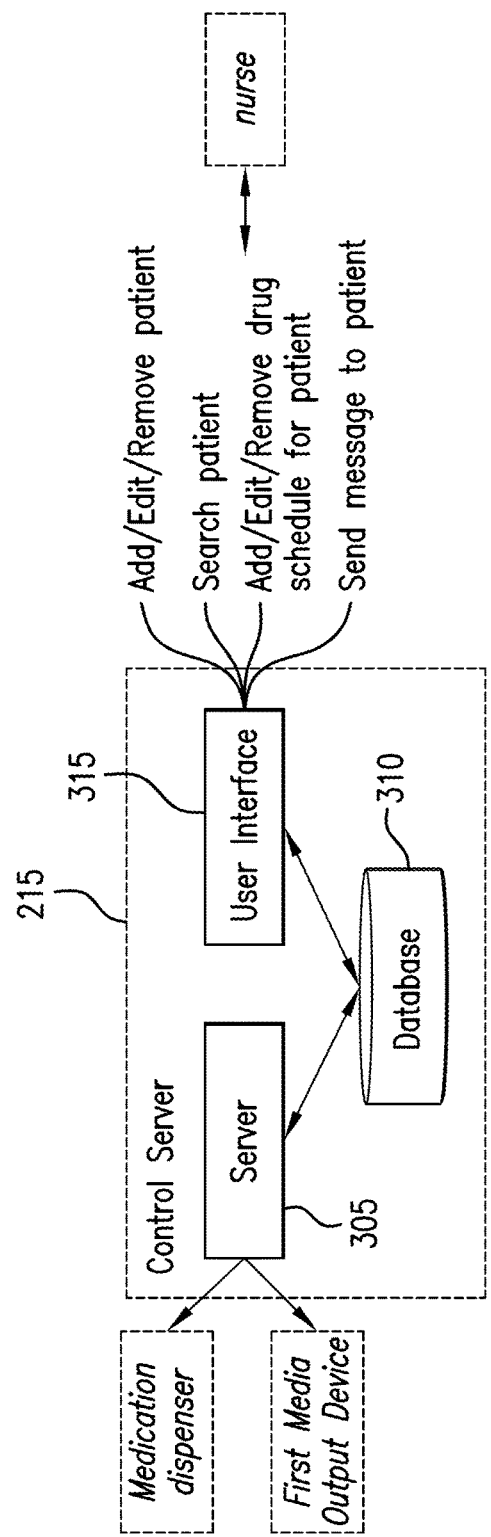
FIG. 3 presents a schematic diagram illustrating a control server that a patient care provider can interact with to connect to a remote patient for monitoring according to one or more implementations of the present invention.

With reference now to FIGS. 2-3, control server 215 is a general purpose computer implementing specific software and having a database that allows nurses to configure medication delivery schedules and to edit and send messages to patients. In one or more implementations, control server 215 includes a server 305, database 310, and user interface 315, is communicatively coupled to mobile cart 120. For example, via control server 215, a patient care provider can access the user interface 315 to create or edit patient information, search for patients, create or edit patient medication schedules, and send asynchronous messages to the patient. Control server 215 can take such edits to patient information and update saved patient records in database 310 and transmit such new or revised medication schedules and messages to the patient to the mobile cart 120. In one or more implementations, the control server 215 is a general purpose computer with a specific software and database that allows nurses to configure the medication delivery schedules and to edit and send messages to patients.

With reference now to FIGS. 4-7, schematic diagrams of mobile cart 120 and patient monitoring devices associated with the mobile cart are illustrated in accordance with one or more implementations of the present invention. In one or more implementations, the mobile cart 120 is a single, integrated form. In one or more implementations, the mobile cart 120 includes one or more separate members coupled together. For example, the mobile cart can comprise a base having an upper surface and a lower surface, and a support member extending outwardly from the upper surface of the base, in which the support member has one or more storage locations for supporting patient monitoring devices. Storage locations can be shelves, ledges, racks, mantles, channels, vacancies, snap-fits, bolt- or screw-ons, or other attachment points. The storage locations can be located fully within the mobile cart 120 or a component thereof, be housed partially within the mobile cart or component thereof and extend outwardly partially from the mobile cart or component thereof, or be located on an outer surface of the mobile cart or component thereof.

In a particular implementation, mobile cart 120 includes a computing device 405, a first media input device 410, a first media output device 415, one or more patient monitoring sensors 420, a second media output device 425, a medication dispenser 430, and a power supply 435. Each patient monitoring device can be physically supported by the mobile cart at one or more storage locations as provided herein.

Computing device 405 includes at least one processor, a non-transitory processor-readable media (i.e., a memory), and one or more respective data communication subsystems that are each configured to communicate via a respective data communication protocol. The computing device 405 can include, for example, mobile computing devices such as tablet computing devices, smartphones, personal digital assistants or the like, as well as laptop computers and/or desktop computers. By way of example, computing device 405 may be personal computers such as Intel Pentium-class and Intel Core-class computers or Apple Macintosh computers, tablets, smartphones, but are not limited to such computers. Other computing devices which can communicate over a global computer network such as palmtop computers, personal digital assistants (PDAs) and mass-marketed Internet access devices such as WebTV can be used.

The processor of computing device 405 can be one or more microprocessors and connected system components (e.g., multiple connected chips) or the computing device may be a system on a chip. The processor can comprise a single processor, multiple discrete processors, a multi-core processor, or other type of processor(s) known to those of skill in the art, depending on the particular implementation. In one or more implementations, the processor is coupled to the non-transitory media. The non-transitory media can be used for storing data, metadata, and programs for execution by the processor. The non-transitory media can include one or more of volatile and non-volatile memories, such as Random Access Memory ("RAM"), Read Only Memory ("ROM"), Flash, Phase Change Memory ("PCM"), or other type. The computing device 405 coordinates the interactions of the various components of the mobile cart 120 through one or more software modules implemented by the processor. Occasionally, the computing device 405 may be referred to simply as a processor.

In one or more implementations, the one or more respective data communication subsystems include a first data communication subsystem that provides for network data communications with at least one computing device that is located remotely from the mobile cart and a second data communication subsystem that provides for data communications for patient monitoring devices supported by the mobile cart. Computing device 405 has the ability to send and receive data across network 130, and can be integrated with cameras, microphones and software applications, including web browsers or other applications various implementations.

Via the first data communication subsystem, the computing device 405 can coordinate data transfer of measured vital sign data and captured media data via the mobile cart 120 to the patient care provider system 105 across network 130. In one or more implementations, the first data communication subsystem includes a router 710 and a mobile telecommunications modem 720. The router 710 can be configured by the processor of computing device 405 to establish a secure VPN channel between the patient-side and health care provider over a network 130. For example, the router 710 can be a Mikrotik router configured to automatically negotiate the VPN connection without additional user interaction upon receiving power (such as plugging in mobile cart 120 to an AC outlet). Mobile telecommunications modem 720 can be any modem as is known in the art that is configured to connect to and transmit data across a mobile telecommunications network (e.g., network 130). In one or more implementations, modem 720 is a 3G/4G modem. In one or more implementations, the first data communication subsystem can facilitate asynchronous messaging between the patient and the health care provider.

Via the second data communication subsystem, the computing device 405 can communicate with and coordinate data transfer among patient monitoring devices at the mobile cart (e.g., first media input device 410, first media output device 415, sensors 420, second media output device 425, etc.). For example, sensors 420 can sense a patient vital sign and transmit a signal representing the patient vital sign to the processor of the computing device 405 via the second data communication subsystem, in which the signal is processed to thereafter display audio and/or visual content associated with the vital sign at second media output device 425. In one or more implementations, computing device 405 can be communicatively coupled to computing devices located remotely from mobile cart 120. For example, such remote computing devices can be associated with the patient care provider or hospital.

In one or more implementations, the first data communication subsystem and the second data communication subsystem are the same. In one or more implementations, the first data communication subsystem and the second data communication subsystem are different.

In addition, the hardware arrangement of the present invention is not limited to devices that are physically wired to network 130, and wireless communication can be provided among the components of mobile cart 120, as well as between computing device 405 and patient care provider system 105. In one or more implementations, the present application provides improved processing techniques to prevent packet loss, to improve handling interruptions in communications, and other issues associated with wireless technology.

It will be appreciated that additional components, not shown, may also be part of the computing device 405, and, in certain implementations, fewer components than that shown in the Figures may also be used in computing device 405. It will be apparent from this description that aspects of the inventions may be embodied, at least in part, in software. That is, the computer-implemented methods may be carried out in a computer system or other data processing system in response to its processor or processing system executing sequences of instructions contained in a memory, (e.g., one or more protocols) such as the non-transitory processor-readable media of computing device 405 or other machine-readable storage medium. The software may further be transmitted or received over a network via a network interface device. In various implementations, hardwired circuitry may be used in combination with the software instructions to implement the present implementations. Thus, the techniques are not limited to any specific combination of hardware circuitry and software, or to any particular source for the instructions executed by the computing device 405.

A first media input device 410 is provided to capture media (e.g., video and audio) at the patient's location (e.g., at mobile cart 120). The media input device 410 is operatively connected to at least one processor via at least one data communication system. The media input device 410 includes at least one camera 411 configured for capturing video, and at least one microphone 412 configured for capturing audio. The camera 411 and microphone 412 can be combined in a single structure at one storage location at mobile cart 120, or can be separately supported at particular storage locations at the mobile cart. In a particular arrangement, the camera 411 is one or more camera or image processing devices. The camera 411, in accordance with one implementation, is a video camera designed to capture color video of objects within the field of view of the camera. In one arrangement, the camera 411 is integral to the processor, such as with an integrated camera of a smartphone or other computing device. In a further implementation, the camera 411 is an "off the shelf" digital camera or web-camera that is connected to the processor using standard interfaces such as USB, FIREWIRE, Wi-Fi, Bluetooth, and other wired or wireless communication technologies suitable for the transmission video data. The camera 411, in one non-limiting implementation, includes an integrated microphone 412 such that a separate microphone is not needed. In one or more implementations, in which microphone 412 includes one or more microphones, the plurality of microphones cooperate with one another to capture audio. For example, a particular microphone can be limited to capture sounds at a particular decibel range or frequency.

In one or more implementations, media input device 410 streams captured video and/or audio directly to a remote computing device (e.g., nurse video conference device 210) in a continuous, substantially real-time way. In one or more implementations, media input device 410 records video and/or audio to a local or remote storage (e.g., via cloud store or at control server 215).

In one or more implementations, the media input device 410 is in connection with a first media output device 415 (e.g., as a video conferencing system). First media output device 415 can include a display and an audio speaker. In one more implementations, the first media input device 410 and the first media output device 415 are combined into a single structure. For example, a combined first media input/output device can be those sold by LIFESIZE, which allows the monitoring system 100 to have complete control over the quality of video conferencing between the patient and the remote health care provider, without additional infrastructure.

The first media output device 415 is operatively connected to at least one processor via at least one of the data communication systems and is configured to output video and audio content through the display and the audio speaker. Output video and audio content can include media captured locally (e.g., by first media input device 410), or media received via the first data communication subsystem from a computing device that is located remotely from the mobile cart. For example, remote video and audio content can be transmit and displayed at first media output device 415 over network 130 by a patient care provider via nurse video conferencing system 210. The display of first media output device 415 can be of any type suitable for outputting multimedia data and for user interaction as provided herein. For example, the display can be an organic light-emitting diode ("OLED"), light-emitting diode ("LED"), LED matrix or similar display types. In a particular implementation, the display is a LED (light emitting diode) display having a true color 24 bit LED monitor. In a further implementation, the display is a touch-screen display (e.g., resistive touch input panel, capacitive input panel, or other haptic display). The touch screen can include a stylus or other input device for making annotations directly onto the display. Other displays provided herein may be of the same or similar type as first media output device 415.

In one or more implementations, a patient can initiate a video conference with a remote patient care provider via the computing device 405 that is transmitted by one or more data communication subsystems. For example, the patient or the remote patient care provider can send a request to open a video conference session at any time in which, if the corresponding party accepts, a real-time video communication conference is opened. In one or more implementations, if the remote patient care provider initiates the video conference, the computing device 405 must accept the request to initiate video conferencing. In one or more implementations, either the patient or the remote patient care provider can send asynchronous messages to the other party that is displayed on first media output device 415. Asynchronous messages can be automatically displayed patient-side without requiring patient acknowledgement or action. Such messages can consist of text, images or video containing useful information and care advice.

Figure 4:
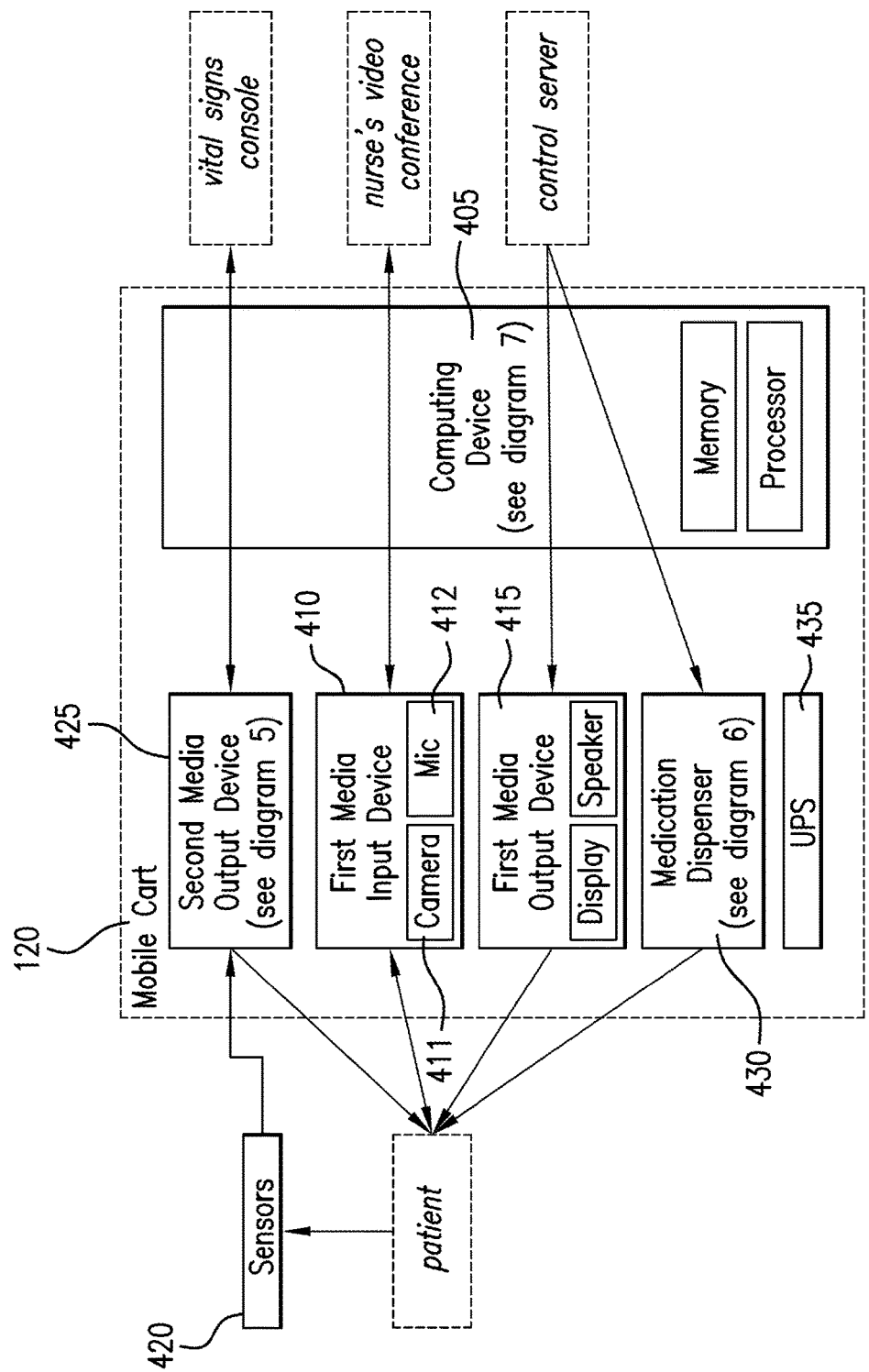
FIG. 4 presents a schematic diagram illustrating a patient-side mobile cart for remotely monitoring a patient according to one or more implementations of the present invention.
Figure 5:
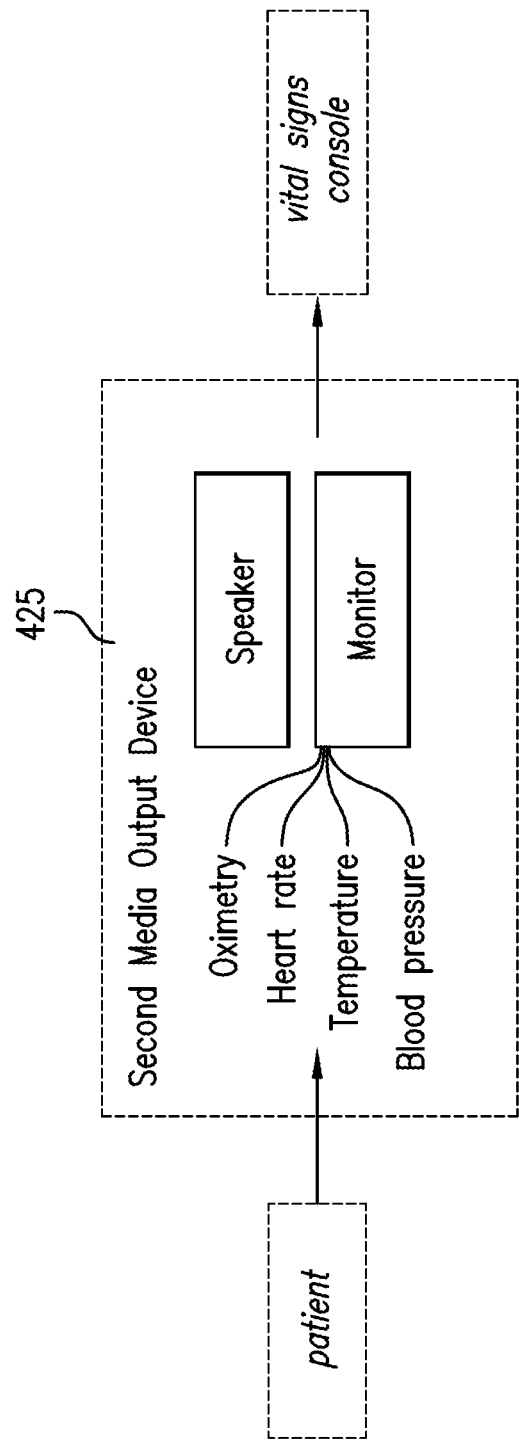
FIG. 5 presents a schematic diagram illustrating a media output device for a mobile cart according to one or more implementations of the present invention.

With reference now to FIGS. 4-5, in one or more implementations, mobile cart 120 includes at least one patient monitoring sensor 420 and a second media output device 425 for measuring patient vital signs and displaying the status of such vital signs on one or more output devices (e.g., vital signs monitoring), either locally or remotely in a continuous, substantially real-time stream. For example, mobile cart 120 can be configured to measure vital signs including, but not limited to oximetry, heart rate, temperature, blood pressure, respiratory rate, and pulse. The patient monitoring sensor 420 is configured to interface with a patient, to sense a patient vital sign and to transmit a signal representing the patient vital sign to the processor via at least one of the data communication subsystems. The patient monitoring sensor 420 can be a biosensor or mechanical sensor as are known in the art, such as arm bands, pulse oximeters, and blood pressure cuffs. In one or more implementations, the sensor 420 can be a single sensor or one or more sensors capable of measuring one or more vital signs. In one or more implementations, sensor 420 is mechanically connected to mobile cart 120. For example, sensor 420 can be operatively connected with second media output device 425. In one or more implementations, sensor 420 is physically separate from mobile cart 120. For example, sensor 420 can be a wireless sensing device which transmits patient vital signs wirelessly to the mobile cart 120, such as to the second media output device 425.

Second media output device 425 includes at least one display and at least one audio speaker. In or more implementations, the vital sign signal corresponding to a measured vital sign that is transmitted to the processor of computing device 405 via the first data communications subsystem, in which the computing device processes the signal and instructs the second media output device 425 to display audio and visual content associated with the measured vital sign information. For example, the display can show a value corresponding to the patient's current heart rate (e.g., 80 beats per minute), or emit a sound corresponding to the rhythm of the patient's heartbeat.

In one or more implementations, the mobile cart 120 can measure the patient's current health vital signs and transmit such information to the patient care provider system 105 across the network 130 in a continuous, substantially real-time fashion. For example, the processor can process vital sign information sensed by the patient monitoring sensors, and then immediately transmit, via the first data communications subsystem, the data to vital signs console 205, where it is displayed on a monitor that can be viewed by a nurse. In this way, the patient does not have to instruct the mobile cart 120 to send vital signs data as long as the patient is connected to the patient monitoring sensors 420, as the above disclosed devices can communicate directly with the health service provider-side system 105 without any type of hub in between. Thus, the monitoring system 100 is capable of monitoring acute, post-chirurgical patients that require real time monitoring over a period of time. This improves upon conventional remote vital sign monitoring, in which a particular vital sign is measured and gathered information is transmitted to a wireless (e.g., Bluetooth) hub that concentrates all measurements and forwards them to a central system when an Internet connection is available. Such an approach is unsuitable beyond chronic patients that must send vital signs a few times a day to control conditions that do not require real-time monitoring, such as hypertension, diabetes, or obesity.

Figure 6:
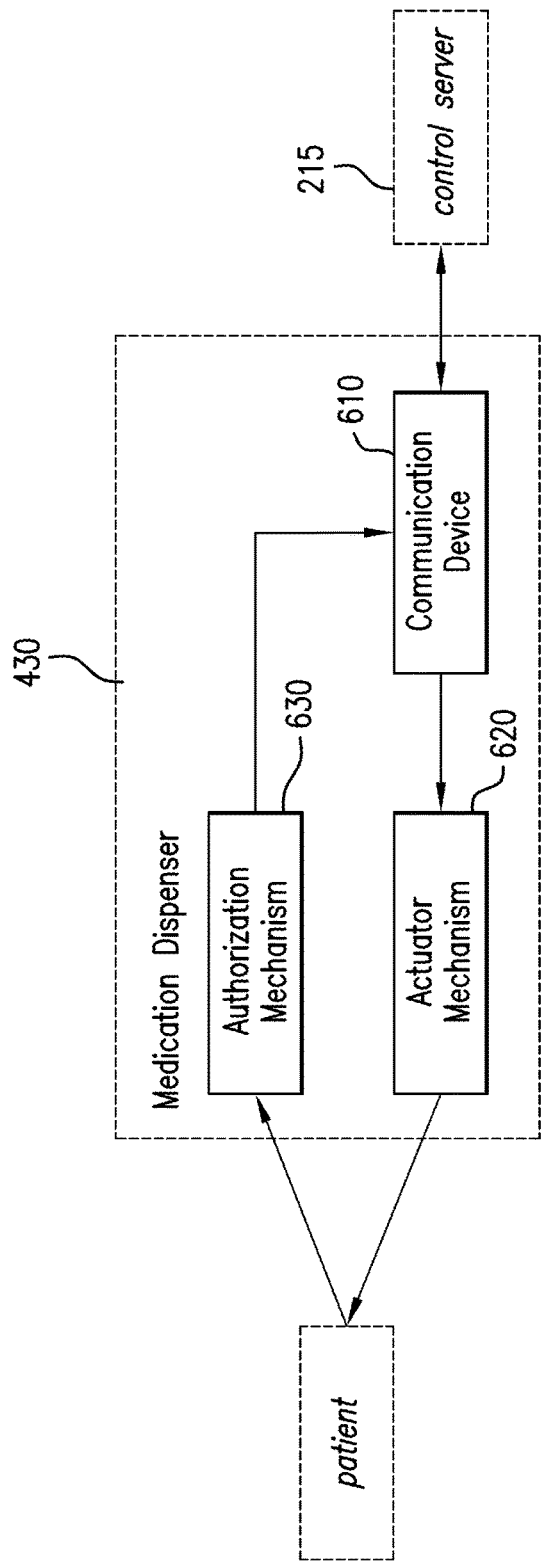
FIG. 6 presents a schematic diagram illustrating a medication dispenser for a mobile cart for remotely monitoring a patient according to one or more implementations of the present invention.
Figure 7:
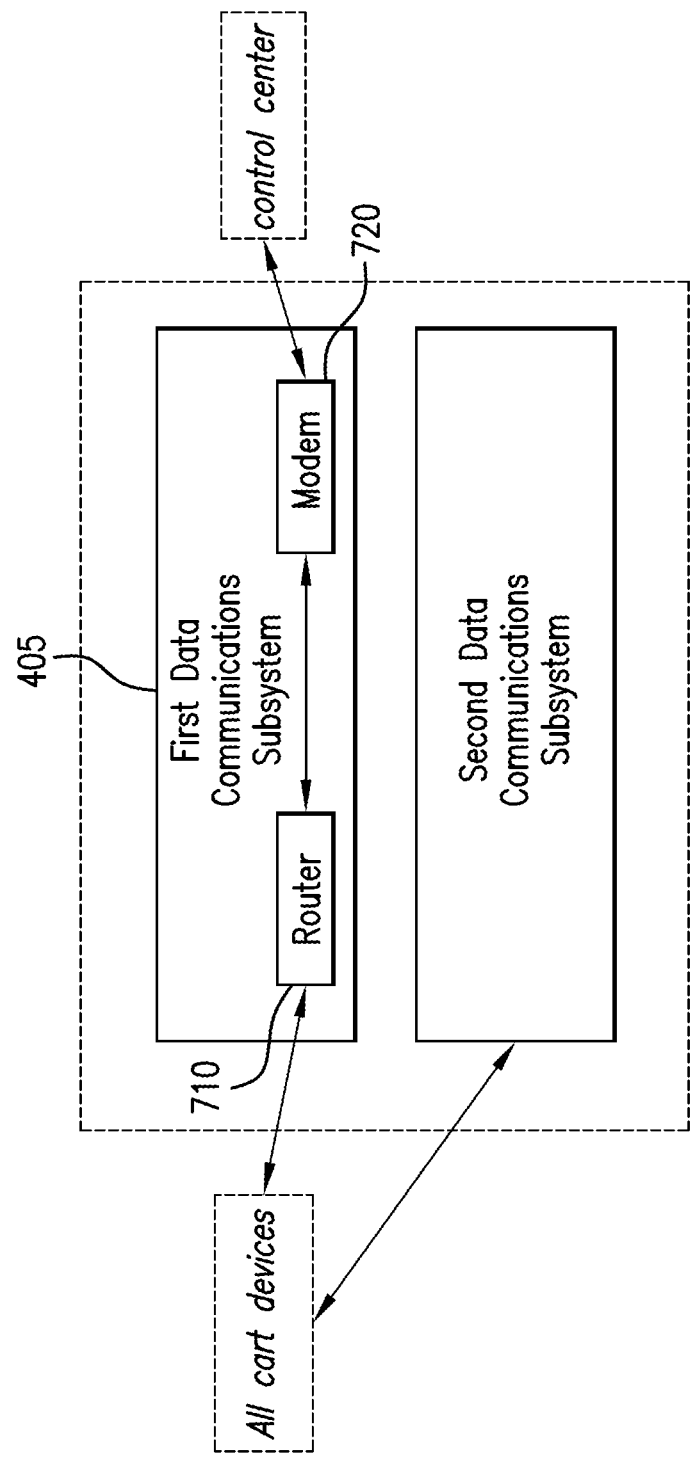
FIG. 7 presents a schematic diagram illustrating a computing device for a mobile cart for remotely monitoring a patient according to one or more implementations of the present invention.

With reference now to FIGS. 4 and 6, in one or more implementations, a medication dispenser 430 is provided at the mobile cart 120. The medication dispenser 430 is operatively connected to the processor via the at least one or more of data communication subsystems. In one or more implementations, the medication dispenser 430 can be autonomous from the other components of mobile cart 120, or it can be integrated with other components, such as the media output devices 415, 425. In one or more implementations, the processor of computing device 405 implements program code concerning a medication dispensing module to provide alerts to the patient upon occurrence of one or more scheduled events. For example, the patient can be alerted that it is time to take medication daily, weekly, or other times, such as in response to measured vital signs or a measurement of patient pain. In one or more implementations, the alerts can be initiated or programmed remotely, such as by control server 215. In one or more implementations, the medication dispenser 430 further includes a communication device 610 which can implement one or more data communication subsystems without requiring communication with computing device 405. Communication device 610 can be a data receiver, processor or other device that is capable of receiving pre-programmed medication schedules from a remote machine (e.g., control server 215)

In one or more implementations, the medication dispenser 430 is integrally formed with a surface of the mobile cart 120 such that an opening and a corresponding lid are the only external portions that are accessible by a patient. The lid is adjustable between a closed position (i.e., the patient cannot reach into the opening) and an open position (i.e., the lid is retracted and the opening is free). In one or more implementations, the medication dispenser 430 includes a locking mechanism for locking the lid into a closed position. For example, the lid can be secured by a latch, bolt, lock, or other locking component as is known in the art.

Medication dispenser 430 can include one or more internal chambers containing medication that are not accessible without authorization. For example, though the opening and lid are patient-facing, to refill a prescription, an authorized medication distributor, such as a doctor or nurse, must fill the internal chambers. Access to internal medication chambers can be restricted by an additional lock at the mobile cart 120.

In one or more implementations, medication dispenser 430 includes an actuator mechanism 620 configured to control the lid to move between the closed position and the open position. For example, the actuator mechanism 620 can comprise motors, gears, locking pins or bars, latches, spring loaded assemblies, latches, or other similar mechanisms suitable for moving a lid from a closed to an open position and vice versa.

In one or more implementations, after a scheduled alert has occurred at the mobile cart 120 the actuator mechanism can also dispense a medication to the patient after an authorization mechanism 630 confirms that the patient is authorized to receive the medication.

If the communication device 610 receives a scheduled alert, a patient must complete an authentication service via authorization mechanism 630 to verify patient identity to cause the actuator mechanism 620 to dispense medication. Patient authentication can be accomplished via a username and password service, a numerical personal identification number (PIN) or use of biometric identifier devices. For example, the biometric identifier can include one or more fingerprint identification devices. In an alternative or further combination, the biometric identifier can include an iris scanner, facial recognition camera, voice recognition technology, and/or other biometric identification devices. The biometric identifier can provide a secure, authenticated environment by requiring validation of data from one or more biometric readings, such as fingerprint analysis, facial recognition, iris recognition, retinal scanning, voice identification. For example, an individual might have to verify his or her fingerprint pattern, or speak a passcode in order to connect to the system 100. In the event that authorization mechanism 630 verifies a patient's identity, then a scheduled medication is delivered by actuator mechanism 620. If the authorization mechanism 630 is unable to verify the patient identity, then it can notify the patient care provider. For example, the authorization mechanism 630 will be unable to verify identity if the biometric identification does not result in a match (e.g., a different fingerprint), or if the patient puts in an incorrect password after multiple attempts.

In one or more implementations, the medication dispenser 430 can implement a notification mechanism for transmitting a notification (e.g., via the secure VPN channel) to the patient care provider if the medication has been dispensed by actuator mechanism 620, expiration of a pre-determined time limit, or the authorization mechanism 630 being unable to confirm that the patient is authorized to receive the medication. The pre-determined time limit can be measured from when the scheduled alert is generated. For example, if the patient does not collect the medication within a number of minutes or an hour, the processor will instruct a notification to be sent to the health care provider to alert a doctor, nurse, or other care giver that the patient is late in following a medication schedule. Such notifications can be in textual or other formats, as is known in the art. In one or more implementations, the medication dispenser 430 can generate notifications if the quantity of one or more medications to be dispensed is exhausted. In one or more implementations, the medication dispenser 430 scheduling process can be in combination with EMR management. For example, the medication dispensing module can be configured to adjust electronic medical records stored in a database at the health care provider-side if a particular patient's medication schedule changes.

Mobile cart 120 can be powered by an uninterruptible power supply (UPS) 435. The UPS 435 can be of the on-line, line-interactive, or standby types, as is known in the art. In one or more implementations, the UPS 435 includes a two- or three-pronged plug for connection to a patient-side power source (e.g., an outlet).

Figure 8:
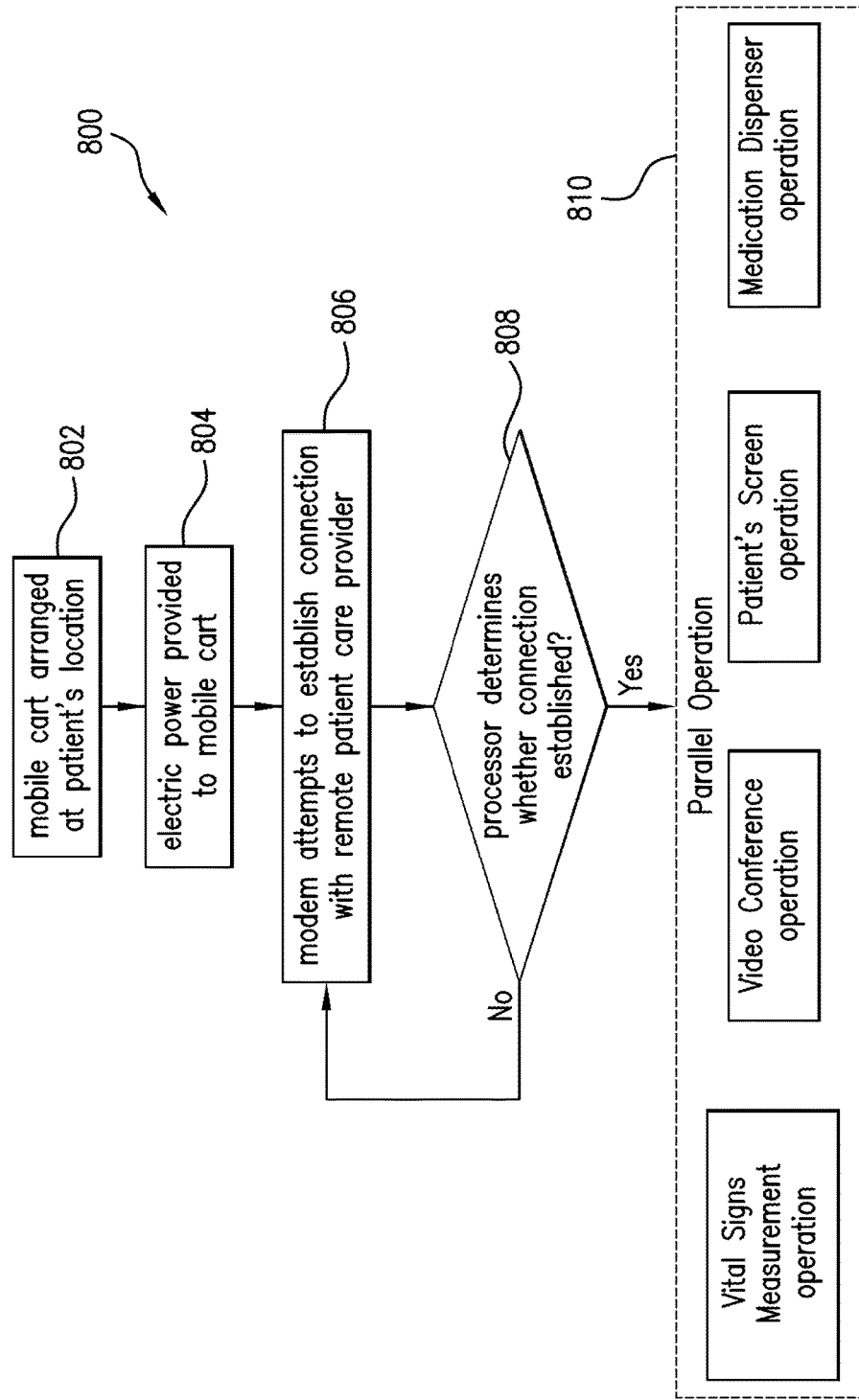
FIG. 8 presents a flow diagram illustrating a method for operating a patient-side mobile cart for remotely monitoring a patient according to one or more implementations of the present invention.

With reference now to FIG. 8, a method flow 800 for operating a patient-side system according to one or more implementations is provided. In this exemplary method flow, the patient-side system is mobile cart 120. The method 800 begins at step 802 in which the mobile cart is arranged at the patient's location. For example, if mobile cart 120 is used, the cart can be wheeled to the patient's bedside. The patient's location can be the patient's home, an assisted living care center, a bed in a hospital, or other similar places. In one or more implementations, no additional infrastructure beyond electric power and sufficient space to house the patient system is required. At step 804, electric power is provided to the mobile cart. For example, the mobile cart can connect a two- or three-pronged plug into a local AC power outlet to power the various devices at the cart. Upon receiving power, a mobile telecommunications modem (e.g., modem 720) attempts to establish a network connection with a remote patient care provider computing device at step 806. A processor (e.g., the processor of computing device 405) determines whether a connection has been established. A network connection can be established, for example, with a remote patient care provider-side system and a corresponding control center (e.g., control center 110) therein. If the processor determines that the modem is unable to establish a connection, the method loops to step 806 and the modem attempts to establish a connection again. However, if the processor determines that the modem is able to establish a connection, then the mobile cart becomes fully operational. A fully operational mobile cart can perform further method flows in parallel or separately, depending on the desired operations, step 810. For example, a fully operational mobile cart can perform vital signs measurements, video conferencing, patient/patient care provider messaging, and medication dispensing functions simultaneously, or separately.

Figure 9:
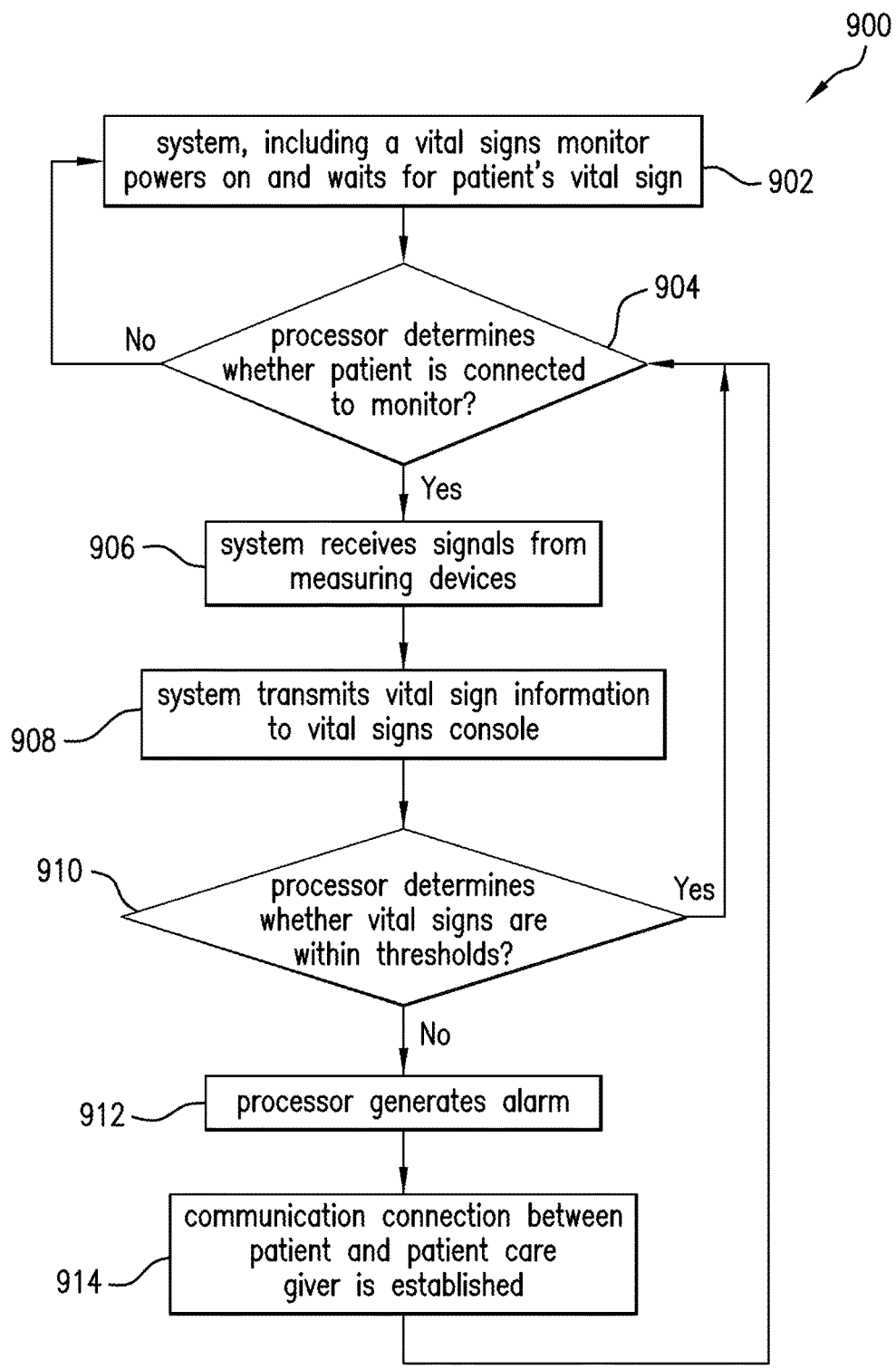
FIG. 9 presents a flow diagram illustrating a method for measuring patient vital signs for a remote patient according to one or more implementations of the present invention.

With reference now to FIG. 9, a method flow for a system for measuring patient vital signs information 900 according to one or more implementations is provided. According to method 900, a fully operational and powered cart also powers a vital signs monitor. A vital signs monitor can be an audiovisual output device (e.g., second media output device 425) comprising a display and an audio speaker, in conjunction with one or more patient monitoring sensors (e.g., sensors 420) that interface with a patient. In one or more implementations, a processor (e.g., the processor of computing device 405) is operatively connected with the vital signs monitor, via one or more data communication subsystems. In one or more implementations, the vital signs monitor is communicatively connected with a remote vital signs console in order to transmit vital signs remotely in a continuous, substantially real-time manner. For example, the vital signs monitor can be in connection with vital signs console 205 at a hospital.

The method 900 begins at step 902 in which the system, including a vital signs monitor, is powered on and idles while waiting for a vital sign signal. A vital sign is a measurement of the status of a patient's vital (i.e., life-sustaining) functions. Vital signs can include, but are not limited to: body temperature, blood pressure, heart rate, respiratory rate, and pulse oximetry. In one or more implementations, the vital signs monitor can have a default mode which conserves power. For example, if a particular vital sign signal is not being received, the vital signs monitor can limit the available functions, such as by not displaying values associated with such particular vital signs. At step 904, a processor determines whether a patient is connected to the vital signs monitor. If the processor determines that a patient is not connected to the vital signs monitor, then the method loops to step 902 and continues to wait for a patient vital sign measurement. However, if the processor determines that a patient is connected to the vital signs monitor, then at step 906, system receives signals respective to the vital signs from patient monitoring sensors (e.g., patient monitoring sensors 420) or other patient measuring devices. In one or more implementations, if the patient monitoring sensors measure a patient vital sign, the processor instructs the vital signs monitor to display values associated with vital signs measurements (via one or more media output devices). For example, if the patient monitoring sensors measure a patient's temperature, the vital signs monitor displays that temperature on a display.

In one or more implementations, the system of method 900 includes a remote connection to patient care provider system (e.g., patient care provider system 105). While this method is described at times in the context of an interaction with a nurse at a hospital, the method is not limited to a nurse/hospital and patient interaction, as caregivers located at different patient care providers (e.g., an assisted living center) can implement the method 900. At step 908, the system transmits vital sign information to a remote vital signs console. For example, the processor, via the first data communication subsystem, transmits vital signs measured by the patient monitoring sensors to a remote vital signs console. At step 910, a processor determines whether the measured vital signs are within predetermined thresholds. In one or more implementations, the processor is a remote processor, such as control server 215. In one or more implementations, the processor implements program code indicating what vital sign measurement thresholds are acceptable for humans. For example, an acceptable body temperature threshold can be set to be between 97.6-99.6 degrees Fahrenheit. If the processor determines that the vital signs are within acceptable thresholds, then the method loops to step 904 and continues to measure the patient vital signs. However, if the processor determines that one or more vital signs are not with acceptable thresholds, at step 912, the processor generates an alarm. The alarm can be generated by vital signs console 205 and can be alert a patient care provider to the change in vital signs. In one or more implementations, the method continues at step 914, and a communication connection between the patient care provider system and the patient system is established. For example, nurse video conferencing system 210 can request a video conference with the patient system. In one or more implementations, the patient care provider system requests an audio call with the patient's caretaker. In one or more implementations, such video or audio conferencing is automatically initiated by the processor. Thereafter, the method loops to step 904.

Figure 10:
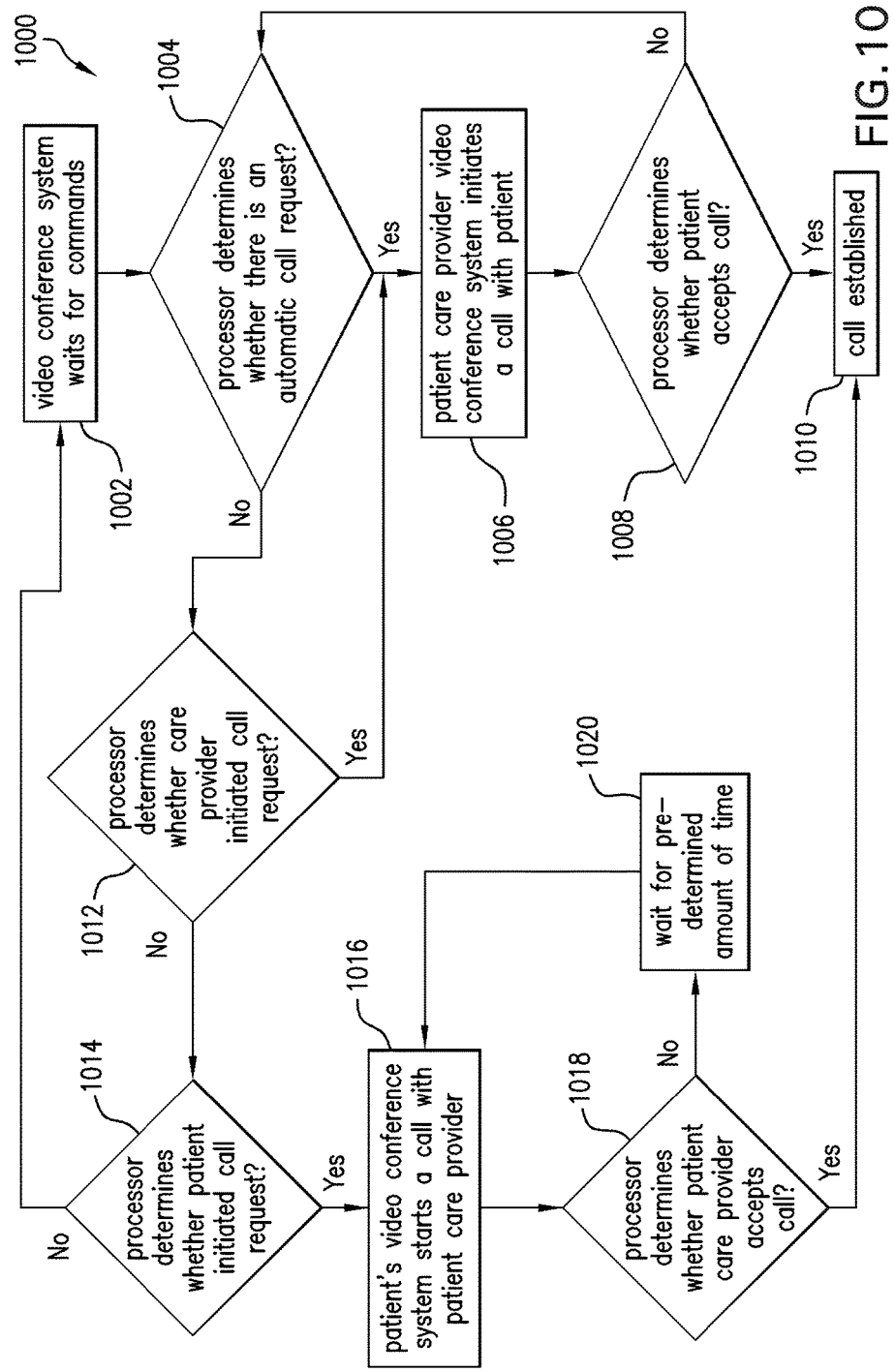
FIG. 10 presents a flow diagram illustrating a method for video conferencing with a remote patient according to one or more implementations of the present invention.

With reference now to FIG. 10, a method flow for video conferencing between a patient care provider and a remote patient 1000 according to one or more implementations is provided. While this method is described at times in the context of an interaction with a nurse at a hospital, the method is not limited to a nurse/hospital and patient interaction, as caregivers located at different patient care providers (e.g., an assisted living center) can implement the method 1000. The method begins at step 1002, in which a video conferencing system idles and waits for a command. In one or more implementations, the video conferencing system is nurse video conference 210, media input device 410, media device 415, or a combination of these elements. At step 1004, a processor determines whether an automatic call request has been made. The processor can be located at, for example, computing device 405, control server 215, or a combination of the two. An automatic call request can be via video, audio, text, or a combination thereof. In one or more implementations, an automatic call request is made in response to receiving a vital sign signal indicating that a patient's vital signs are outside of acceptable thresholds (as in steps 912-914). If the processor determines that an automatic call request has been made, then at step 1006, the patient care provider video conference system initiates a call with the patient system. In one or more implementations, the patient system (e.g., mobile cart 120) will broadcast video and/or audio alerts. For example, the patient system can ring, flash lights, vibrate, or perform other notification techniques, as is known in the art. Next, a processor determines whether the patient has accepted the automatic call request, step 1008. The patient can accept the call by pressing a button at the patient side, speaking a passcode, or otherwise interfacing with a control (such as via a user interface) at the system. In one or more implementations, the automatic call request will be available for acceptance for a pre-determined time limit. If the processor determines that the patient has not accepted the call request, then the method loops to step 1004. If the processor determines that the patient accepted the call, then at step 1010, the call is established between the patient care provider and the patient. In one or more implementations, the call can be transmitted across via a secure VPN channel.

However, if the processor determines that there has not been an automatic call request at step 1004, the method branches to step 1012, and the processor determines whether a nurse or other care provider at the patient care provider side has initiated a call request. In one or more implementations, the nurse can initiate a call request by interfacing with nurse video conferencing system 210. Such interfacing can be done through a user interface, via touch screens, or other input devices (e.g., keyboard and mouse) as is known in the art. For example, a nurse may want to contact the patient to inform the patient of a change in medication scheduling. If the processor determines that the nurse has initiated a call request, then the method branches to step 1006. If the processor determines that the nurse has not initiated a call request, then the method branches to step 1014, and determines whether the patient has initiated a call request to the patient care provider side. The patient can initiate a call request through input devices included at a corresponding patient-side video conferencing system, for example, at mobile cart 120 via computing device 405, media input device 410 and media output device 415. In one or more implementations, the patient can initiate a call via a user interface, via touch screens, or other input devices (e.g., keyboard and mouse) as is known in the art. If the processor determines that the patient has initiated a call request, then the patient system connects to the patient care provider system and begins a call between the parties, step 1016. In one or more implementations, the patient care provider must accept the call request. In one or more implementations, the patient call request is automatically accepted by the patient care provider. For example, the patient care provider may have a representative available 24 hours a day in order to handle patient call emergencies. At step 1018, the processor determines whether the patient care provider system or representative (e.g., a nurse) accepts the call request. If the processor determines that the patient care provider has yet to accept the call, the method branches to step 1020 and waits a pre-determined amount of time. For example, the time to accept the call request may be 10 seconds, and then the connection is closed. The method branches to step 1016 thereafter. However, if the patient care provider system or the patient care provider representative accepts the call, the method branches to step 1010 and establishes a call between the parties.

Figure 11:
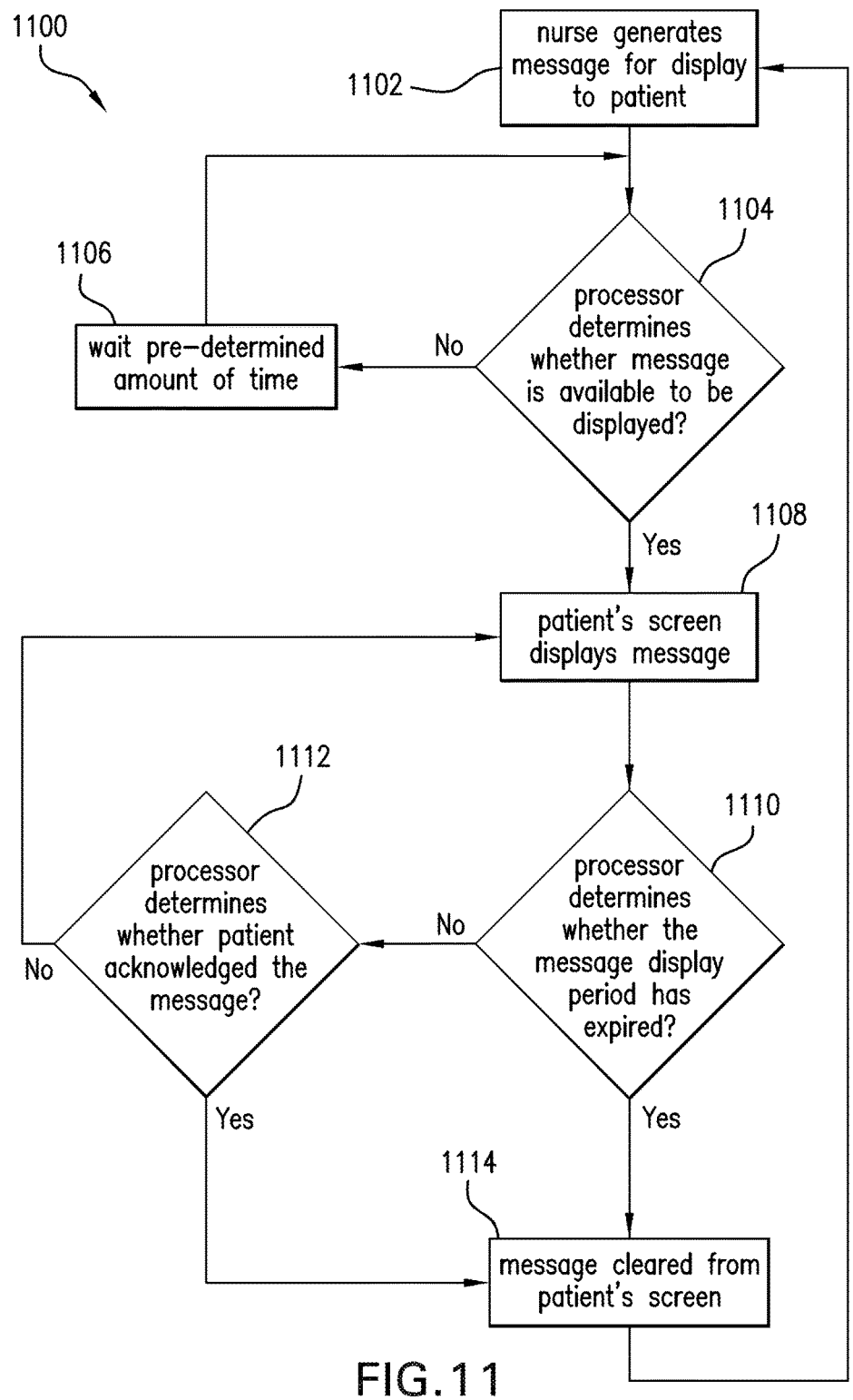
FIG. 11 presents a flow diagram illustrating a method for asynchronous messaging between a patient care provider and a remote patient according to one or more implementations of the present invention.

With reference now to FIG. 11, a method flow for asynchronous messaging between a patient care provider and a remote patient 1100 according to one or more implementations is provided. At times, either the patient care provider or the patient may determine that immediate communication is not necessary and may opt to transmit video, audio, or textual messages to the other party for later viewing. In one or more implementations, messages are transmitted across a mobile telecommunications network. In one or more implementations, if the patient care provider-side system or the patient-side system is unable to connect to a network, messages can be created and saved for transmission until the next time the system connects to the network. Method 1100 is described in terms of a unilateral message delivery method from a patient care provider representative (e.g., a nurse) to the patient; however the method is not limited to messaging in only one direction. A similar or the same method can be applied for the patient to deliver asynchronous messages to the patient care provider.

The method 1100 begins at step 1102 in which a nurse generates a message to be displayed at a remote patient's media output device. For example, the message can be displayed at first media output device 415. In one or more implementations, the nurse can set a specific delivery time for the message. In one or more implementations, after message generation, the nurse instructs a patient care provider system (e.g., control server 215 of patient care provider system 105) to transmit the message across a network. Next, a processor determines whether a message is available for display, step 1104. For example, the processor associated with computing device 405 monitors incoming messages via one or more data communication subsystems. If no message is available to be displayed, the method branches to step 1106, and the processor waits a pre-determined amount of time before checking for new messages. For example, the processor can wait 10 seconds, 30 seconds, 1 minute, or other timeframes. After the pre-determined timeframe expires, the method then loops to step 1104 and checks for new messages. If the processor determines that there is a new message to be displayed, then at step 1108, the processor instructs the message to be displayed at a patient-side display. For example, the patient-side display can first media output device 415. In one or more implementations, the message is displayed for a pre-determined display time period. In one or more implementations, the patient or other patient-side party (e.g., the patient's caretaker) must select a control at the patient system to clear the message. At step 1110, the processor determines whether the message display period has expired. If the display period has not expired, the processor determines whether the patient or other patient-side party has acknowledged the message, step 1112. If not, the method loops to step 1108 and continues to display the message. If the processor determines that the display time period has expired, or determines that the patient or other patient-side party has acknowledged the message, then the method branches to step 1114 and the message is cleared from the patient-side display. Thereafter, the method loops to step 1102 and waits for a new message.

Figure 12:
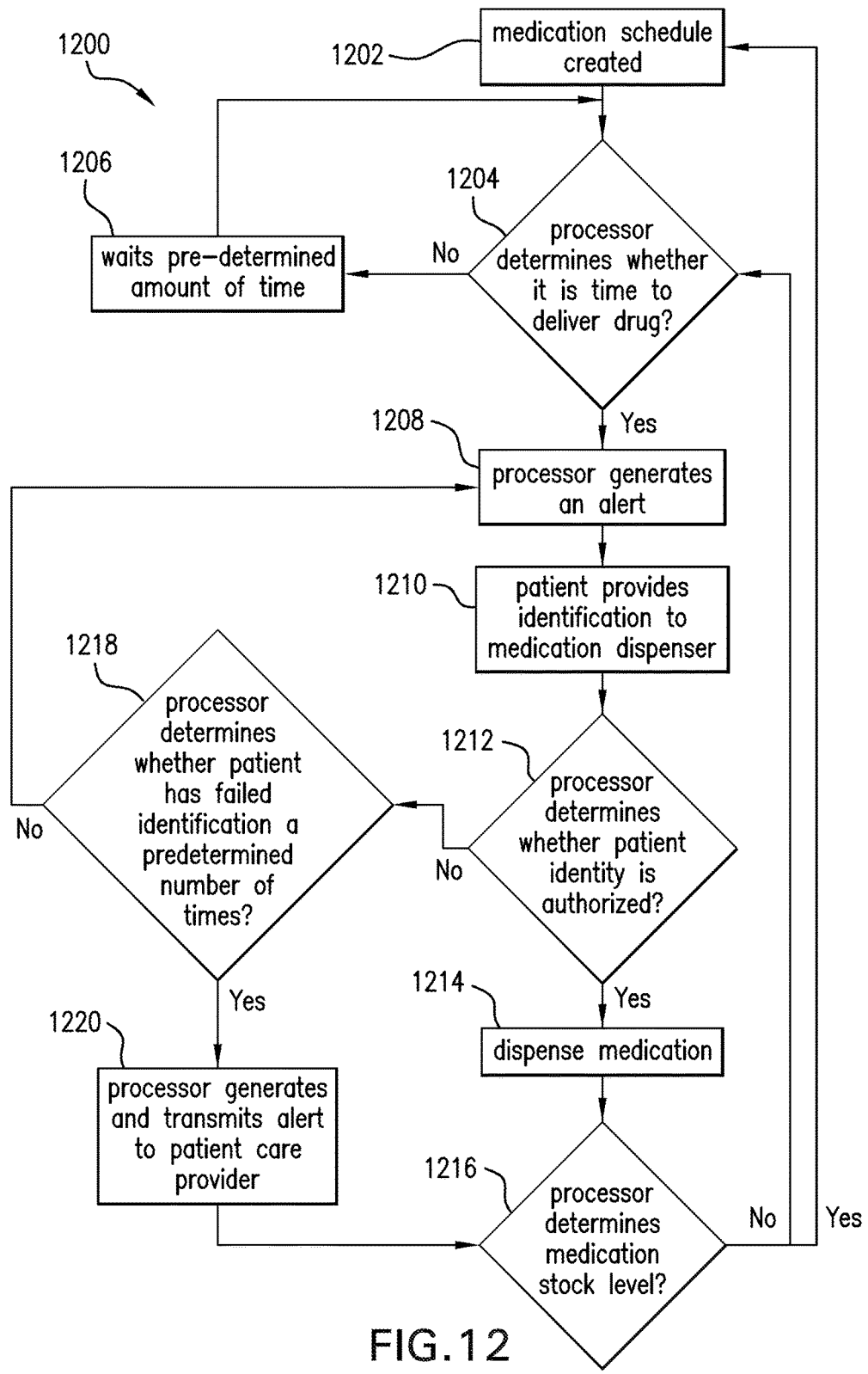
FIG. 12 presents a flow diagram illustrating a method for dispensing medication at a mobile cart for remotely monitoring a patient according to one or more implementations of the present invention.

With reference now to FIG. 12, a method flow for dispensing medication at a remote medication dispenser 1200 according to one or more implementations is provided. Medication is stored locally at the patient side and is dispensed by a medication dispenser (e.g., medication dispenser 430). In one or more implementations, one or more types of medication can be stored at a patient system (e.g., mobile cart 120) and dispensed according to pre-programmed schedules. Such schedules can be set by a patient care provider and adjusted as needed. In one or more implementations, medication dispensing can be in response to changes in measured patient vital signs, such as changes in patient temperature, or identification of increased patient pain. In one or more implementations, medication dispensing can be manually initiated by a patient care provider via one or more methods herein.

Method 1200 begins at step 1202 in which a patient care provider (e.g., a nurse) creates a medication schedule for a patient. A medication schedule includes the particular times that a patient should take a particular medication. The medication schedule can be a pre-programmed schedule created by one or more processors implementing program code in order to control operation of the medication dispenser. For example, a patient may need to take a blood pressure medication three times a week at a certain time (e.g., 2 pm). In one or more implementations, a medication schedule can be automatically updated at the patient-side as the patient care provider modifies the schedule. In one or more implementations, the medication dispenser is filled with one or more medications. This can be done by a nurse or approved patient caretaker. At step 1204, the processor determines whether medication should be delivered to the patient according to the medication schedule. If the processor determines that it is not time to deliver the medication, then the method waits a pre-determined time, step 1206. The pre-determined time can be, for example, 10 seconds, 30 seconds, 1 minute, or other time periods. Thereafter, the method loops to step 1204.

However, if the processor determines that it is time to deliver the medication according to the medication schedule, then the method branches to step 1208 and the processor generates an alert. For example, the processor alerts the patient that it is time for a medication delivery. In one or more implementations, the processor implements program code to instruct an alert mechanism to alert the patient. For example, the alert can include audio alerts, flashing lights, vibrations, or other alert methods, as are known in the art. Next, the patient provides identification to the medication dispenser for authorization, step 1210. In one or more implementations, authorization is achieved via biometric identifiers, mechanical identifiers, name/password combinations, or PIN numbers. For example, a patient can place his or her finger on a fingerprint scanner to verify patient identity.

At step 1212, the processor determines whether the patient identity is authorized. In one or more implementations, authorization can include matching patient bioidentifiers to a database of authorized users. If the processor determines that the identified patient is authorized to receive medication, then the method branches to step 1214 and the processor instructs the medication dispenser to dispense medication. In one or more implementations, the processor instructs an actuator mechanism to unlock a lid restricting access to the medication. Thereafter, the method, at step 1216, determines the medication stock level. If the medication stock level is below a refill threshold, the method notifies the patient care giver that the medication needs to be refilled and the method branches to step 1202. If the medication stock level is above the refill threshold, then the method branches to step 1204.

However, if the method is unable to identify an authorized patient, in one or more implementations, the method notifies the patient that identification produced an unauthorized user and requests identification again. The patient can then attempt identification again. At step 1218, the processor determines whether the patient has failed the identification process a predetermined number of times. For example, the method may allow a patient three or four attempts at verifying identity. If the patient successfully identifies himself or herself as an authorized user upon a further attempt, then the method branches to step 1208. However, if the processor determines that the patient has failed identification the predetermined number of times, then the method branches to step 1220 and alerts the patient care provider that the patient associated with the particular medication has failed to produce an authorized identity. Thereafter the method branches to step 1216.

Figure 13C:
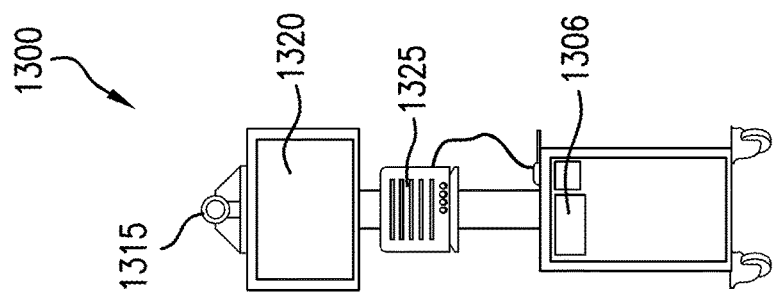
FIG. 13C presents a front view of the exemplary embodiment of a system for remotely monitoring patients of FIG. 13A.
Figure 13B:
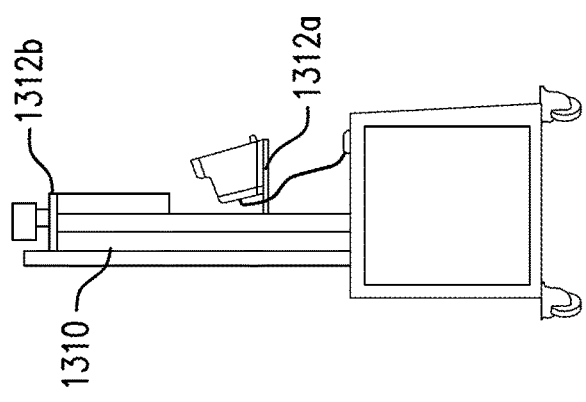
FIG. 13B presents a side view of the exemplary embodiment of a system for remotely monitoring patients of FIG. 13A.
Figure 13A:
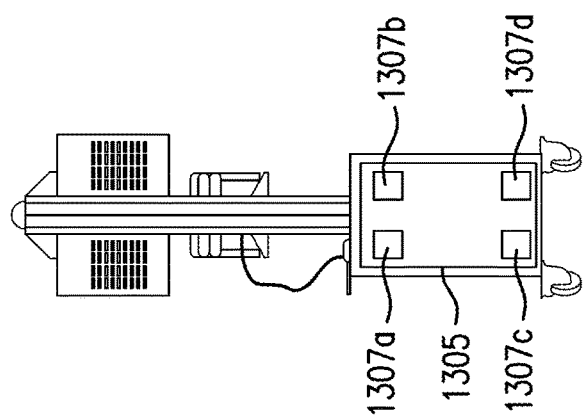
FIG. 13A presents a back view of an exemplary embodiment of a system for remotely monitoring patients.

With reference now to FIGS. 13A-13C, an example implementation for remotely monitoring patients is illustrated in the form of a mobile wheeled cart 1300. Mobile cart 1300 is designed for compactness, robustness and easy transportation, yet is still ergonomic and easy for caregivers and patients to use, even while in bed. The mobile cart 1300 includes a base 1305 having one or more wheels connected to a bottom surface of the base. The wheels can have independent swivel parts to provide lateral movement for the cart in all directions. The base in one or more implementations is a rectangular or trapezoidal prism, although other shapes can be used depending on implementation. The base can function as a cabinet or storage for various components of the patient monitoring system such as, for example, computing device 405, medication dispenser 430, and UPS 435. Patient monitoring system components can be disposed entirely within the housing of the base 1305, partially within the housing and partially extending outwardly from the housing, or be attached to an outer surface of the base. In the example mobile cart 1300, a computing device and power supply are fully contained in the housing of the base and a medication dispenser 1306 is located partially within the base 1305 such that an opening covered by a lip is the only accessible portion via the outer surfaces of the base. In one implementation, the base is 620 mm by 550 mm by 340 mm.

To facilitate airflow, the base 1305 can have exhaust vents 1307*a*, 1307*b*, 1307*c*, 1307*d* formed through its outer surface and/or fans or heatsinks (not shown) disposed within the base. A support member 1310 extends from an upper surface of the base 1305. The support member 1310 can have one or more shelves, ledges, racks, mantles, channels, vacancies, or attachment points (collectively "storage locations" 1312*a*, 1312*b*) disposed along its length. In one or more implementations, the storage locations are positioned perpendicular to the longitudinal axis of the support member 1310. In the example implementation of mobile cart 1300, a first media input device 1315, a first media output device 1320, a second media output device 1325 are positioned along the support member 1310 on shelves. In the example implementation, the first media input device 1315 includes a combined camera and microphone, and is in connection with the first media output device 1320 to display video and audio captured either patient-side, remotely (such as at a patient care provider), or both (e.g., for video conferencing). The second media output device 1325 can be a display for measuring patient vital signs in conjunction with patient monitoring sensors (not shown). The height of such components may be designed such that the second media output device 1325 and first media output device 1320 can be seen by a patient prone in bed without having to stand-up and move. Each of the components of mobile cart 1300 can be dissembled, though the unit is designed to be compact and carried as a single unit. For example, the mobile cart 1300 can have dimensions of 1530 mm×490 mm×550 mm.

Mobile cart 1300 does not require any setup or configuration once it is located at patient-side and connected to a power source. Any number of mobile carts 1300 can be connected to a remote central station at a health care provider without loss of functionality.

FIGS. 1 through 13C are conceptual illustrations allowing for an explanation of the present invention. Those of skill in the art should understand that various aspects of the implementations of the present invention could be implemented in hardware, firmware, software, or combinations thereof. In such implementations, the various components and/or steps would be implemented in hardware, firmware, and/or software to perform the functions of the present invention. That is, the same piece of hardware, firmware, or module of software could perform one or more of the illustrated blocks (e.g., components or steps).

In software implementations, computer software (e.g., programs or other instructions) and/or data is stored on a machine-readable medium as part of a computer program product, and is loaded into a computer system or other device or machine via a removable storage drive, hard drive, or communications interface. Computer programs (also called computer control logic or computer readable program code) are stored in a main and/or secondary memory, and implemented by one or more processors (controllers, or the like) to cause the one or more processors to perform the functions of the invention as described herein. In this document, the terms "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like.

Notably, the figures and examples above are not meant to limit the scope of the present invention to a single implementation, as other implementations are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an implementation showing a singular component should not necessarily be limited to other implementations including one or more the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific implementations will so fully reveal the general nature of the invention that others can, by applying knowledge within the skill of the relevant art(s) (including the contents of the documents cited and incorporated by reference herein), readily modify and/or adapt for various applications such specific implementations, without undue experimentation, without departing from the general concept of the present invention. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various implementations of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary implementations, but should be defined only in accordance with the following claims and their equivalents.

What is claimed:

1. A mobile patient communication and medication delivery system to monitor health of a patient, deliver medication to the patient, and facilitate communication between the patient and a remotely located patient care provider, comprising:

a mobile cart including at least one storage location for supporting patient monitoring devices, the patient monitoring devices including:

a computing device supported by the mobile cart and including at least one processor, non-transitory processor-readable media, and one or more respective data communication subsystems that are each configured to communicate via at least one respective data communication protocol, wherein a first of the data communication subsystems provides for network data communications with at least one computing device that is located remotely from the mobile cart, and a second of the data communication subsystems provides for data communications for patient monitoring devices supported by the mobile cart;

a mobile telecommunications modem and a router that is configured to establish a secure VPN channel automatically upon receiving power;

at least one media input device including at least one of a camera and a microphone, the at least one media input device being operatively connected to the at least one processor via at least one of the data communication systems;

a first media output device supported by the mobile cart and operatively connected to the at least one processor via at least one of the data communication systems, the first media output device including at least one display and at least one audio speaker, and configured to provide at least one of audio and visual content received via the first data communication subsystem from the at least one computing device that is located remotely from the mobile cart;

at least one patient monitoring sensor configured to interface with a patient, to sense a patient vital sign and to transmit a signal representing the patient vital sign to the processor via the second data communication subsystem;

a second media output device supported by the mobile cart and operatively connected to the at least one processor via at least one of the data communication systems, the second media device including at least one display and at least one audio speaker, and configured to automatically provide at least one of audio and visual content associated with the patient vital sign; and a medication dispenser supported by the mobile cart, the medication dispenser being operatively connected to the processor via at least one of the plurality of data communication subsystems, wherein in response to receiving the signal from the sensor, the at least one processor processes the signal and substantially in real-time and without human intervention, securely transmits across the secure VPN channel by the first communication subsystem, each of: at least one of the captured audio and visual content and the processed vital sign signal, to the at least one computing device that is located remotely from the mobile cart.

2. The mobile patient communication and medication delivery system according to claim 1, further comprising an identification mechanism that is a biosensor.

3. The mobile patient communication and medication delivery system according to claim 2, wherein the biosensor is one of: a fingerprint identification device, an iris scanner, a facial recognition camera, or a voice recognition device.

4. The mobile patient communication and medication delivery system according to claim 1, further comprising an identification mechanism that is a user id and password login system.

5. The mobile patient communication and medication delivery system according to claim 1, the medication dispenser comprising:
an alert mechanism to alert the patient to receive a medication,
an authorization mechanism to confirm that the patient is authorized to receive the medication;
an lid configured to move between a closed position and an open position, wherein the open position enables access to an opening in the medication dispenser, and further wherein the closed position prevents access to the opening;
an actuator mechanism configured to control the lid to move between the closed position and the open position, and to dispense a medication to the patient after the authorization mechanism confirms that the patient is authorized to receive the medication; and a notification mechanism that is configured to transmit a notification to the patient care provider via the secure VPN channel after at least one of the medication being dispensed, expiration of a pre-determined time limit, and the authorization mechanism being unable to confirm that the patient is authorized to receive the medication.

6. The mobile patient communication and medication delivery system according to claim 5, wherein the alert mechanism activates in response to a pre-programmed delivery schedule.

7. The mobile patient communication and medication delivery system according to claim 5, wherein the alert mechanism activates in response to a change in a vital sign.

8. The mobile patient communication and medication delivery system according to claim 5, wherein the alert mechanism activates in response to an indication of pain by the patient.

9. The mobile patient communication and medication delivery system according to claim 5, wherein the alert mechanism comprises one or more LED lights.

10. The mobile patient communication and medication delivery system according to claim 5, wherein the alert mechanism comprises an audio speaker operatively connected to the first data communication subsystem.

11. The mobile patient communication and medication delivery system according to claim 1, wherein the vital sign measured by the at least one patient monitoring sensor includes at least one of: respiratory rate, oximetry, heart rate, temperature, and blood pressure.

12. The mobile patient communication and medication delivery system according to claim 1, wherein the mobile cart comprises a base and a support member coupled to a top surface of the base and extending outward from the base.

13. The mobile patient communication and medication delivery system according to claim 12, wherein the mobile cart comprises one or more wheels coupled to a bottom surface of the base.

14. The mobile patient communication and medication delivery system according to claim 1, wherein the at least one storage location is a shelf.

15. The mobile patient communication and medication delivery system according to claim 1, further comprising a patient care provider-side system including a control center and an electronic medical records system communicatively coupled together.

16. The mobile patient communication and medication delivery system according to claim 15, wherein the control center comprises a vital signs console, a nurse video conferencing system, and a control server, wherein the control server includes a server, a database, and a user interface.

17. The mobile patient communication and medication delivery system according to claim 1, wherein the first data communication subsystem and the second data communication subsystem are the same.

18. The mobile patient communication and medication delivery system according to claim 1, wherein the first data communication subsystem and the second data communication subsystem are different.

19. A method for monitoring health of a patient and delivering medication to the patient, comprising:
communicatively coupling a patient-side computing device including at least one processor and non-transitory processor-readable media to a patient care provider computing device located remote to the patient-side computing device, via one or more respective data communication subsystems that are each configured to communicate via at least one respective data communication protocol, wherein a first of the data communication subsystems provides for network data communications with at the remote computing device, and a second of the data communication subsystems provides for data communications for patient monitoring devices at the patient-side;

sensing a patient vital sign, via at least one patient monitoring sensor configured to interface with the patient;

transmitting a signal representing the patient vital sign to the processor via the first second data communication subsystem;

determining, by the processor, whether a patient vital sign value corresponding to the signal representing the patient vital sign falls within an acceptable threshold; and in the event that the patient vital sign falls outside of the acceptable threshold, dispensing medication to the patient via a medication dispenser operatively connected to the processor, wherein the dispensing medication step comprises:
  generating an alert that it is time for the patient to receive a medication,
  authorizing the identity of the patient,
  enabling access to the medication dispenser,
  dispensing medication, and
  automatically establishing, via the first data communication subsystem, a secure VPN communication connection with the patient care provider computing device after at least one of the medication being dispensed, expiration of a pre-determined time limit, and being unable to confirm that the patient is authorized to receive the medication.

20. The method of claim 19, further comprising:
processing, by the processor, the signal representing the patient vital sign, to generate at least one of audio and visual content associated with the patient vital sign; and
displaying at least one of audio and visual content associated with the patient vital sign at a media output device.

21. A method of monitoring health of a patient, and facilitating communication between the patient and a remotely located patient care provider, according to claim 19, wherein the establishing a communication connection comprises:
capturing, at the patient-side, at least one of audio and visual content via at least one of a camera and a microphone;
transmitting, by the processor via one or more data communication systems, at least one of audio and visual content to the remote patient care provider computing device;
displaying at the patient provider-side, via a media output device at least one of audio and visual content generated by the patient-side;
capturing, at the patient care provider-side, at least one of audio and visual content via at least one of a camera and a microphone;
transmitting, by the processor via one or more data communication systems, at least one of audio and visual content to the patient-side computing device;
displaying at the patient side, via a media output device at least one of audio and visual content generated by the patient care provider-side,
wherein the preceding capturing, transmitting, and displaying steps occur substantially in real-time and without human intervention.

\* \* \* \* \*